(12) United States Patent
Powell

(10) Patent No.: US 8,287,569 B1
(45) Date of Patent: Oct. 16, 2012

(54) MODULAR SYSTEM AND METHOD FOR FIXATION OF SPINOUS PROCESSES

(76) Inventor: N. Garrett Powell, Nashville, TN (US)

(*) Notice: Subject to any disclaimer, the term of this patent is extended or adjusted under 35 U.S.C. 154(b) by 643 days.

(21) Appl. No.: 12/272,413

(22) Filed: Nov. 17, 2008

Related U.S. Application Data

(60) Provisional application No. 61/003,223, filed on Nov. 15, 2007.

(51) Int. Cl.
*A61B 17/70* (2006.01)
(52) U.S. Cl. .................................. 606/248; 606/250
(58) Field of Classification Search .............. 606/60, 606/246, 248–253
See application file for complete search history.

(56) References Cited

U.S. PATENT DOCUMENTS

| | | | | |
|---|---|---|---|---|
| 7,591,837 B2* | 9/2009 | Goldsmith | ................ | 606/247 |
| 7,922,750 B2* | 4/2011 | Trautwein et al. | ........... | 606/279 |
| 2008/0243186 A1* | 10/2008 | Abdou | ..................... | 606/246 |
| 2008/0281359 A1* | 11/2008 | Abdou | ..................... | 606/246 |

* cited by examiner

*Primary Examiner* — Ellen C Hammond
(74) *Attorney, Agent, or Firm* — Waddey & Patterson, P.C.; Mark J. Patterson; Matthew C. Cox

(57) ABSTRACT

A modular system for fixation of a spinous process includes at least one pair of blocks shaped so as to engage a particular segment of the spinous process and arranged on opposing sides of the spinous process. Each block has a surface facing the portion of the spinous process to be engaged, the surface having an array of sharp spikes to penetrate the spinous process when so engaged. Two rods arranged parallel to the spinous process are provided to connect the at least one pair of blocks and therefore stabilize multiple segments of the spinous process. Each block includes an aperture within a central portion of the block and shaped so as to slidably receive one of the rods. Set screws are provided so as to securely position the block along the length of the rod.

19 Claims, 4 Drawing Sheets

MODULAR SYSTEM AND METHOD FOR FIXATION OF SPINOUS PROCESSES

CROSS-REFERENCES TO RELATED APPLICATIONS

This application claims benefit of the following patent application(s) which is/are hereby incorporated by reference: U.S. Provisional Patent Application No. 61/003,223, filed Nov. 15, 2007.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The present invention relates generally to a system and method for fixation of a spinous process. More particularly, this invention pertains to stabilization of the human spine by applying a system and method to the applicable vertebrae of the spinal column.

Systems for spinal fixation and stabilization are well established in a wide variety of embodiments. Examples in which such systems are generally used to apply force to the spinal column include correcting degenerative conditions or deformities, maintaining a proper structural environment in the healing process from traumatic surgery, or providing temporary but secure positioning of the spine to facilitate the implanting of further components for performing the same functions. Where invasive surgery has been performed, the systems are generally intended to reliably maintain such fixation of the treated spinal process post-operatively so that bony fusion of the vertebrae or other equivalent functions may be achieved.

Early systems performing these functions comprised spinous process wiring. These systems were adequate in preventing flexion but led to relatively poor fixation, particularly in the cervical region of the vertebral column, because they still permitted rotation or extension of the affected region to some extent. This mechanical deficiency is particularly apparent in patients having osteoporosis, as one prominent example.

Other fixation systems have been anchored to a portion of the spinal process using lateral bone mass screws. These systems simply screw components directly into the bone to increase stability. Plates or rods may be utilized to fuse adjacent segments of the spine. However, there are additional problems associated with this method. The bone of the spinous process may be too soft to maintain immobility of the process over time and with increased activity. The method carries some attendant risk of major complications such as vertebral artery or root nerve injury. Further, lateral mass screw fixation systems are technically demanding and therefore may be quite inconvenient to implant and/or to remove.

More recently, systems have been developed to compress portions of the spinous process by sandwiching the processes between a plurality of plates. These plates are tightened with screws that extend through the plates and may or may not contact the spinous process itself, as desired or necessary under the circumstances. Generally speaking, these processes have improved stability without most of the limitations or inconveniences of the previous systems. However, these systems remain troublesome or inadequate where circumstances require fusion of spinous processes having a variety of dimensions, such as where the affected regions range across multiple bodies of vertebrae. Where subjects of variable sizes are involved such as large adults versus small children the problems may be pronounced further.

What is needed, therefore, is a modular system that may reliably perform the necessary function of stabilizing a portion of the spinous process, and that may flexibly adapt to processes of varying sizes and needs. The system would preferably not require any wiring or screwing in of components directly to the spinous process.

There is a further need that the system be able to stabilize multiple adjacent levels of the spinal column, while allowing for safe, quick and convenient implantation and removal of the system.

BRIEF SUMMARY OF THE INVENTION

In one aspect of the present invention, a modular system for fixation of a spinous process includes a plurality of blocks, each block ideally shaped so as to engage a particular segment of the spinous process. The blocks comprise at least one pair of blocks, with each pair arranged on opposing sides of the spinous process. Each block has a surface facing the portion of the spinous process to be engaged, the surface having an array of sharp spikes or otherwise acicular members. A clamping device may be further provided to perform the preliminary task of compressing the blocks against the spinous process. The spikes may penetrate the spinous process and further stabilize the blocks in place upon the spinous process when the blocks are compressed against the spinous process, by the clamping device or as otherwise provided.

In another aspect of the present invention, two rods are provided for connecting the at least one pair of blocks and therefore stabilizing multiple segments of the spinous process where desired. The rods are arranged substantially parallel to the spinous process. In a particular embodiment of the present invention, each block includes an aperture within a central portion of the block and shaped so as to slidably receive one of the rods. Set screws or equivalent fastening components are provided so as to securely position the block along the length of the rod. In this fashion, two or more pairs of blocks may be maintained against an equivalent number of segments of the spinous process. Further, the system is modular in that the rods may be inserted after the blocks are already in place and compressed against the spinous process, and a variety of block sizes may be utilized where necessary given an equivalent shaped aperture for each size of block.

A cross link is further provided that applies a more permanent compressive force to the rods and by extension to the blocks against the spinous process. After the rods are implanted through the one or more pairs of blocks, the cross link is connected to both of the rods. A compressive or distractive force may then be applied across a given space by adjusting a set screw or other equivalent operations. More than one cross link may be applied where the system is intended to span multiple levels of the vertebral body or any other situation demanding further stability in the application of compressive forces.

Once the cross link has been adjusted so as to achieve the desired amount of torque against the particular segments of the spinous process, the clamping device may be removed from the subject. The cross link therefore operates to maintain positioning of the rods and of the blocks until the desired healing or spinal fusion has taken place, or even for a greater amount of time where applicable or desired.

DETAILED DESCRIPTION OF THE INVENTION

Figure 1:
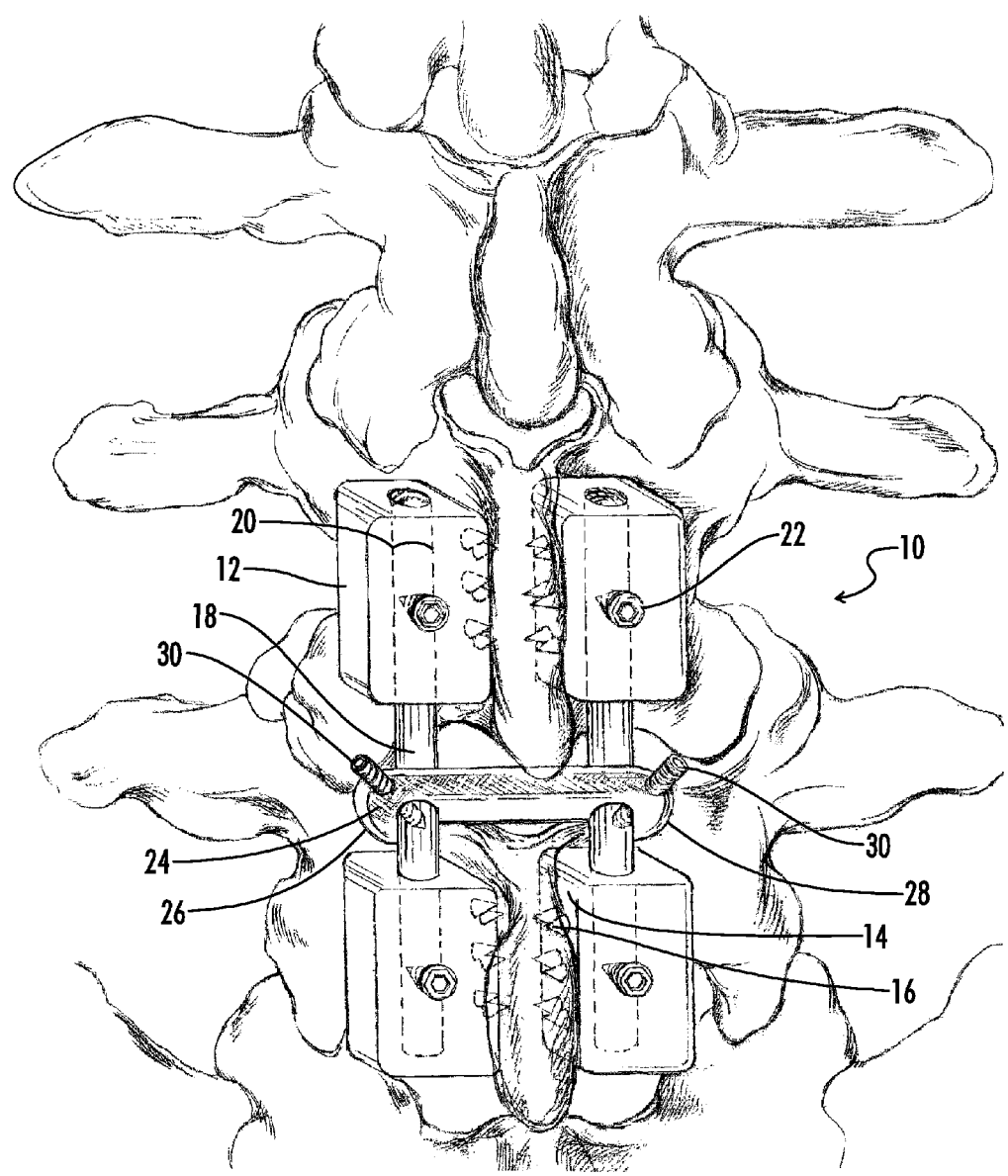
FIG. 1 is a posterior cross-sectional view of a first embodiment of the system of the present invention attached to a portion of a spinal column.
Figures 2, 3:
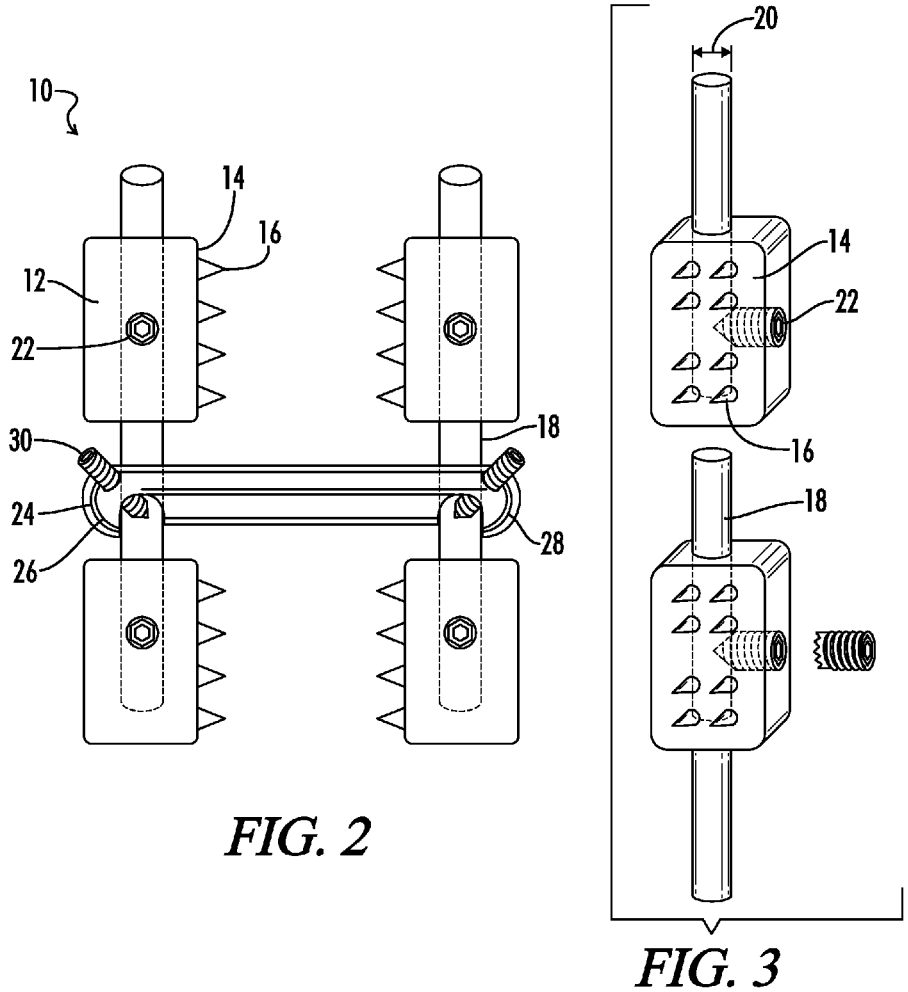
FIG. 2 is a posterior view of the system of FIG. 1 standing alone.
FIG. 3 is a partially exploded side cross-sectional view of blocks and rods of the system of FIG. 1 standing alone.

Referring generally now to FIGS. 1-5, the modular spinous process fixation system 10 of the present invention attaches to one or more particular spinous processes of a spinal column. The system 10 operates to rapidly and efficiently stabilize adjacent levels of the spinal column or vertebral column to allow for fusion or other indicated objectives. The modularity of the system 10 ensures that components are interchangeable to accommodate the variable shapes and sizes of spinous processes located among the separate portions of the vertebral column. Modularity is further desirable to accommodate varying sizes of individuals, such as pediatric patients for example, or spinous processes located within subjects of various states of spinal degeneration or deformity. It is contemplated as well that the system 10 may comprise components of variable length to span one or more interspaces and therefore accommodate the need to stabilize multiple adjacent segments of the vertebral column.

According to one embodiment of the system 10 of the present invention, a plurality of blocks 12 is provided, the blocks 12 being appropriately sized and shaped and having a facing surface 14 intended to operatively engage an associated segment of the spinous process. It is contemplated that the facing surface 14 itself may be designed, for example being grooved, serrated or otherwise roughly composed, such that it engages the spinous process when compressive force is applied and operates to prevent rotation or other undesired movement. However, in preferred embodiments of the present invention the facing surface 14 further comprises an array of acicular members 16. These acicular members 16 will generally comprise sharp spikes 16, but may comprise teeth, serrations or other equivalent protrusions as well. It is contemplated that these spikes 16 may be integral to the blocks 12 or separately attached. The spikes 16 located on the facing surface 14 of each block 12 engage the spinous process and function to better maintain the stability and rigidity of the attachment. The spikes 16 will generally penetrate the bone of the spinous process in question, but this is not a required function.

The blocks 12 comprise at least one pair of blocks 12, with each pair arranged on opposing sides, generally to the left and to the right of the spinous process. The blocks 12 may be scaled in size to accommodate a variety of users such as large adults or pediatric patients. The blocks 12 may be further scaled in size to allow fixation to different parts of the spine, including cervical, thoracic and lumbar segments, or combinations of the above where desired or necessary.

In certain embodiments of the present invention, a clamping device (not herein displayed) may be provided for temporarily compressing each pair of blocks 12 against the spinous process and attaching the system 10 to the affected segments. In this way the system 10 may be assembled during surgical implantation so as to quickly and effectively respond to needs as they arise. It is contemplated that the clamping device may be post-operatively removed once further compressive components or methods have been applied.

In preferred embodiments of the present invention, a pair of elongate members 18 such as rods 18 are provided having equivalent lengths. Each rod 18 is positioned parallel to the affected spinous processes and along a longitudinal axis generally corresponding to that of the spinal column. The lengths of the rods 18 are user-selectable so as to accommodate the entirety of the adjacent spinous processes to be stabilized. The rods 18 may further be adjusted by the surgeon user so as to acquire the desired length, as where needed to span multiple interspaces or to alternatively reduce length where redundant or otherwise unnecessary. This adjustment may be made by physically cutting the rods 18 or other equivalent functions as needed or as available under the associated conditions.

Each block 12 is shaped so as to facilitate attachment to one of the rods 18. In a preferred embodiment of the present invention, each block 12 has an aperture 20 extending at least partially through a central portion of the block 12 along a longitudinal axis, the aperture shaped so as to slidably receive one of the rods 18. Where the aperture 20 extends partially through the block 12, the block 12 may be oriented upon one end of the rod 18 or the opposing end. Where the aperture 20 extends fully through the block 12, the block 12 may be oriented at any position along the length of the rod 18 as desired or necessary under the circumstances.

Figure 4:
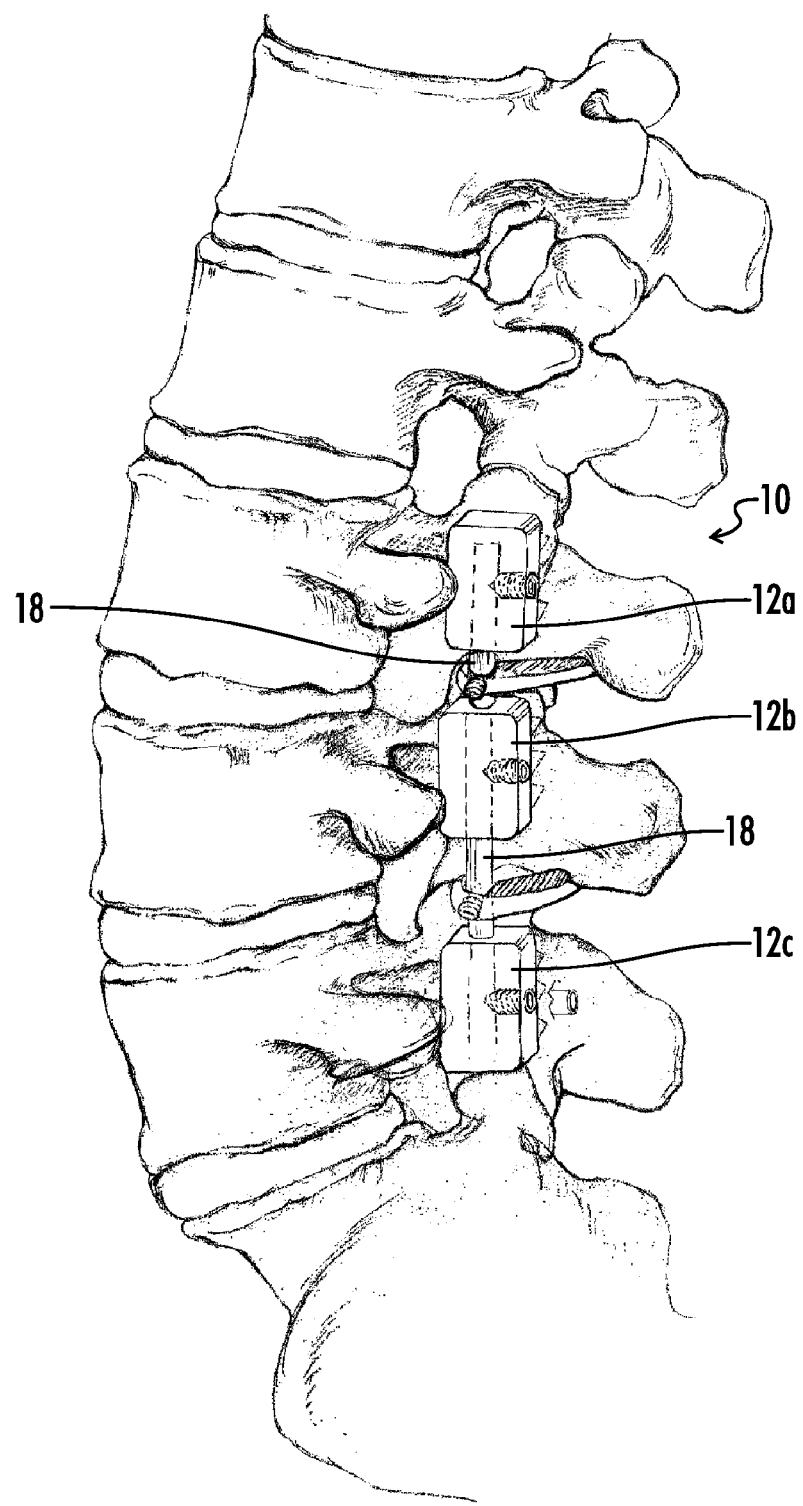
FIG. 4 is a side cross-sectional view of a second embodiment of the system of the present invention attached to a portion of a spinal column, demonstrating more than two blocks oriented along opposing sides of the spinal column.
Figure 5:
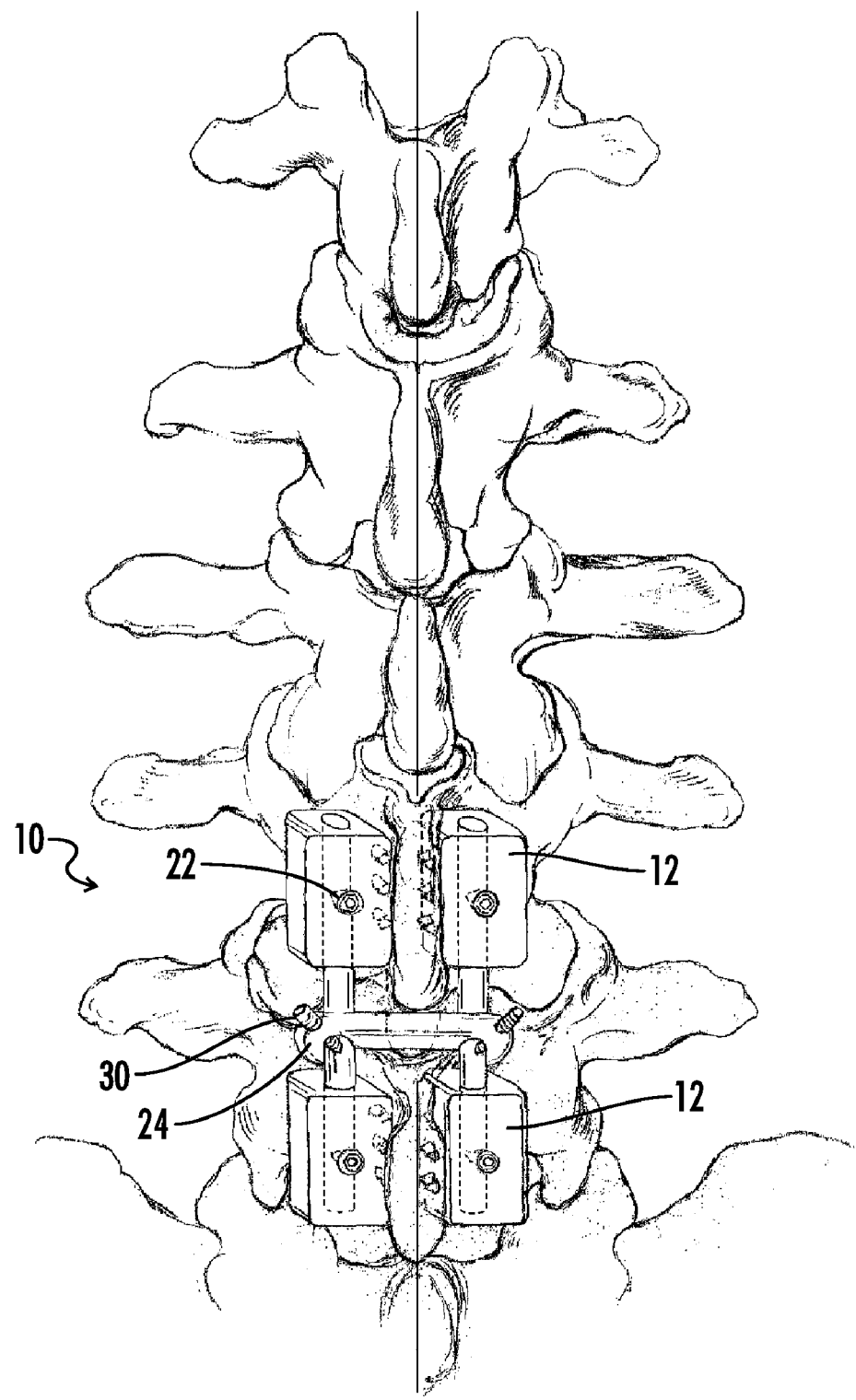
FIG. 5 is a posterior cross-sectional view of the system of FIG. 1 attached to a portion of a spinal column.

Referring to FIG. 4, an embodiment of the present invention is demonstrated wherein first and second blocks 12a, 12c are mounted upon opposing ends of each rod 18, and a third block 12b is further oriented at a third position along the length of each rod 18 between first and second blocks 12a, 12c. This embodiment specifically demonstrates the flexibility of the system 10, as many different levels of the spinal column may be spanned while allowing optimal placement of the blocks 12 on a given spinous process. The system 10 purports to negate the necessity of attaching multiple clamps or blocks 12 onto a single level of the vertebral column.

In the preferred embodiment, each block 12 further comprises a set screw 22 or similar fastening device 22 penetrating the block 12 along a latitudinal axis or otherwise transverse to the axis upon which the aperture 20 is located through which the rod 18 may pass. The set screw 22 operates to tighten the block 12 against the rod 18 when the block 12 has been oriented at a position along the length of the rod 18 as desired by the user or necessary under the circumstances. Various embodiments of tools with which to manipulate the set screws 22 may be contemplated to accommodate the varying conditions under which the system 10 is utilized.

In these embodiments of the present invention, the rods 18 are therefore aligned along the spinous process such that at least one pair of blocks 12 is securely attached to the rods 18. As displayed in FIG. 1, two pairs of blocks 12 are oriented upon opposing ends of the rods 18 and directly upon opposing sides of the spinous process requiring compression. Such compressive force at this juncture may equivalently be applied either against the blocks 12 or the rods 18.

In the preferred embodiment of the present invention, and still referring to FIG. 1, a cross link 24 is further provided that connects to one of the rods 18 on a first end 26 and connects to the other of the rods 18 on a second end 28. A pair of cross link set screws 30 or similar fastening components 30 are angularly oriented upon the first end 26 and the second end 28 of the cross link 24. The set screws 30 may be adjusted in either direction to apply compressive or distractive force against the rods 18 to which the cross link 24 is engaged. In this manner the system 10 may generally be tightened, upon application of each modular component in turn, to a desired level of torque by a user such as a surgeon. Various embodiments of tools with which to manipulate the set screws 30 may be contemplated to accommodate the varying conditions under which the system 10 is utilized.

It other embodiments of the system 10 of the present invention, multiple cross links 24 may be utilized to accommodate variable lengths of rods 18 where many levels of the vertebral column are to be spanned. A separate cross link 24 may be applied at each intervening interspace of the vertebral column. Each cross link 24 may be fixed in length, or adjustable to accommodate variable distances between parallel rods 18.

In embodiments of the present invention comprising the clamping device to preliminarily apply compressive force upon the blocks 12, said clamping device may subsequently be removed upon successful application of the cross link 24.

In particular embodiments of the present invention, the modular components of the system 10, including any of the plurality of blocks 12, the rods 18, the cross link 24, and the set screws 22, 30 are composed of titanium alloy. It is contemplated however that the modular components of the system 10 may alternatively be composed of a metal, polymer, fiber or other alloy or material as desired and as are known within the art.

In an alternative embodiment of the present invention, a method of stabilizing spinous processes within a spinal column is disclosed. At least one pair of spaced blocks 12 is provided to be positioned upon either side of the spinal column, where one or more spinous processes require stabilization. Each block 12 has a surface 14 that is oriented inwardly and generally conforms to the associated segment of the spinous process to be engaged. A plurality of acicular members 16 or spikes 16 are disposed upon the facing surface 14. A first rod 18 is then attached to each block 12 to be positioned along one side of the spinal processes. A second rod 18 is further attached to each block 12 to be positioned along the opposing side of the spinal processes. A cross link 24 or generally a link member 24 is then attached on a first end 26 to the first rod 18 and on a second end 28 to the second rod 18. The user then tightens the link member 24 against the rods 18 to a desired torque so as to securely engage the spinous processes between the blocks 12.

It may be contemplated that many of the steps of the method of this described embodiment of the present invention are performed prior to implantation within the subject. It may be further contemplated that the user seeks to minimize the bulk of the assembly 10 and simplify positioning of the assembly 10 by tightening the cross link 24 as far as possible during implantation of the assembly 10. Distractive force may then be applied to spread the blocks 12 apart immediately prior to physically mounting the assembly 10 upon the spinous processes. The blocks 12 may then be compressed once again so as to drive the spikes 16 into the spinous process and arrive at the desired torque level.

In certain embodiments of the method of the present invention, each pair of blocks 12 may be positioned upon either side of the spinous processes of the subject and clamped in position against each spinous process prior to attaching the rods 18, so as to more effectively maintain the desired position of the blocks 12. In these embodiments, the modular components are generally assembled within the subject.

Upon completion of the step of tightening the link member 24 against the rods 18 to a desired torque, the user may release the initial clamping device and remove said clamping device from the subject.

While the present invention has been displayed and described in some detail in the accompanying description and drawings, these are intended as merely illustrative. Thus, although there have been described particular embodiments of the present invention of a new and useful Modular System and Method for Fixation of Spinous Processes it is not intended that such references be construed as limitations upon the scope of this invention except as set forth in the following claims.

What is claimed is:

1. A modular system for stabilizing one or more spinous processes within a spinal column, the system comprising:
   at least one pair of spaced blocks, each one of said pair of spaced blocks further comprising a facing surface;
   an array of spikes disposed upon each facing surface, wherein each spike is operable to penetrate the spinous process upon compression of the block against the spinous process;
   wherein each block is interchangeably sized and shaped in accordance with the associated spinous process to be engaged;
   wherein for each of the at least one pair of spaced blocks, one block is configured to be positioned upon a first side of the spinous process and the other block is configured to be positioned upon a second side of the spinous process;
   a first rod disposed generally parallel to the spinal column and connected to the one block that is configured to be positioned upon a first side of the spinous process;
   a second rod disposed generally parallel to the spinal column and connected to the other block that is configured to be positioned upon a second side of the spinous process; and
   a cross link having a first end shaped to receive the first rod and a second end shaped to receive the second rod, the cross link operable to compress the spaced blocks against the spinous process;
   wherein at least one block of the pair of spaced blocks comprises an aperture extending entirely through the block, the aperture shaped so as to slidably receive the associated first or second rod, and
   wherein the blocks are secured to the rods with set screws, and wherein the rods are connected to the cross link with set screws.

2. The system of claim 1, wherein the blocks, the rods, the cross link, and the set screws each are further comprised of titanium.

3. A modular system for stabilizing one or more spinous processes within a spinal column, the system comprising:
   at least one pair of spaced blocks, each one of said pair of spaced blocks further comprising a facing surface;
   an array of spikes disposed upon each facing surface, wherein each spike is operable to penetrate the spinous process upon compression of the block against the spinous process;
   wherein for each of the at least one pair of spaced blocks, one block is configured to be positioned upon a first side of the spinous process and the other block is configured to be positioned upon a second side of the spinous process;
   a first rod disposed generally parallel to the spinal column and connected to the one block that is configured to be positioned upon the first side of the spinous process;

a second rod disposed generally parallel to the spinal column and connected to the other block that is configured to be positioned upon the second side of the spinous process; and a plurality of cross links, each cross link having a first end shaped to receive the first rod and a second end shaped to receive the second rod, each cross link being operable to compress the spaced blocks against the spinous process;

two or more each cross link connected to the first and the second rods, wherein at least one block of the pair of spaced blocks comprises an aperture extending entirely through the block, the aperture shaped so as to slidably receive the associated first or second rod.

4. A device for engaging multiple spinous process members in a spinal column for stabilizing a region of a spine, the device comprising:

a pair of spaced rods extending substantially parallel to each other in a longitudinal direction, the pair of rods being configured for positioning on opposite sides of the multiple spinous process members in a longitudinal direction substantially parallel to the spinal column;

a first pair of opposing spaced blocks disposed on a first end of the pair of spaced rods, each of the first pair of opposing spaced blocks including an aperture defined therein, at least one aperture extending entirely through the block, each aperture shaped for slidably receiving one rod of the pair of spaced rods, the first pair of opposing spaced blocks configured for clamping a first one of the multiple spinous process members therebetween;

a second pair of opposing spaced blocks disposed on a second end of the pair of spaced rods, each of the second pair of opposing spaced blocks including an aperture defined therein, at least one aperture extending entirely through the block, each aperture shaped for slidably receiving one rod of the pair of spaced rods, the second pair of opposing spaced blocks configured for clamping a second one of the multiple spinous process members therebetween; and a first cross link member disposed at a location between the first and second pairs of opposing spaced blocks and spanning between the pair of spaced rods in a lateral direction substantially transverse to the longitudinal direction, the cross link member engaging each one of the pair of spaced rods.

5. The device of claim 4, wherein:

each one of the first pair of opposing spaced blocks includes an engagement face having a plurality of spikes extending therefrom configured to directly engage the first one of the multiple spinous process members.

6. The device of claim 5, wherein:

each one of the second pair of opposing spaced blocks includes an engagement face having a plurality of spikes extending therefrom configured to directly engage the second one of the multiple spinous process members.

7. The device of claim 4, wherein:

each block is interchangeably sized and shaped in accordance with the associated spinous process to be engaged.

8. The device of claim 4, wherein:

the first cross link member is configured to apply a compressive force against the pair of spaced rods.

9. The device of claim 4, wherein:

each aperture in each one of the first pair of opposing spaced blocks extends entirely through its respective block in the longitudinal direction.

10. The device of claim 9, wherein:

each one of the pair of spaced rods extends entirely through its associated aperture in the first pair of opposing spaced blocks.

11. The device of claim 9, wherein:

each aperture in each one of the second pair of opposing spaced blocks extends entirely through its respective block in the longitudinal direction.

12. The device of claim 4, wherein:

each block includes a set screw disposed thereon configured to directly engage one of the pair of spaced rods for securing the block at a desired location on the one of the rods.

13. The device of claim 4, wherein:

the first cross link member includes at least two set screws disposed thereon configured to directly engage one of the pair of spaced rods for securing the first cross link member at a desired location on the pair of spaced rods.

14. The device of claim 4, further comprising:

a third pair of opposing spaced blocks disposed on the pair of spaced rods between the first and second pairs of opposing spaced blocks; and each one of the third pair of opposing spaced blocks including an aperture defined entirely through the block, wherein at least one of the third pair of opposing spaced blocks receives one of the pair of spaced rods extending entirely through its aperture.

15. The device of claim 14, further comprising:

the first cross link member disposed between the first and third pairs of opposing spaced blocks; and a second cross link member disposed between the second and third pairs of opposing spaced blocks spanning the pair of spaced rods.

16. A modular apparatus for stabilizing one or more spinous processes within a spinal column, the apparatus comprising:

at least one pair of spaced blocks, wherein one pair of spaced blocks is provided for each of the one or more spinous processes to be stabilized, each of said blocks further comprising a facing surface;

an array of spikes disposed upon each facing surface, wherein each spike is operable to engage the spinous process upon compression of the block against the spinous process;

wherein for the at least one pair of spaced blocks, one block is configured to be positioned upon a first side of the spinous process and the other block is configured to be positioned upon a second side of the spinous process;

a first rod disposed generally parallel to the spinal column and connected to the one block that is configured to be positioned upon a first side of the spinous process;

a second rod disposed generally parallel to the spinal column and connected to the other block that is configured to be positioned upon a second side of the spinous process; and a cross link having a first end shaped to receive the first rod and a second end shaped to receive the second rod, the cross link operable to compress the pair of spaced blocks against the spinous process, wherein at least one block of the pair of spaced blocks comprises an aperture extending entirely through the block, the aperture shaped so as to slidably receive the associated first or second rod.

17. The device of claim 16, wherein:
each block is interchangeably sized and shaped in accordance with the associated spinous process to be engaged.

18. The device of claim 16, wherein:
the at least one pair of spaced blocks, the first and second rods, and the cross-link comprise titanium.

19. The device of claim 16, wherein:
each block of the pair of spaced blocks includes an aperture extending entirely through the block, each aperture shaped so as to slidably receive the associated first or second rod.

* * * * *